United States Patent
Ritson et al.

(10) Patent No.: US 11,534,537 B2
(45) Date of Patent: Dec. 27, 2022

(54) PERITONEAL DIALYSIS SYSTEM AND METHODS

(71) Applicant: OUTSET MEDICAL, INC., San Jose, CA (US)

(72) Inventors: James Ritson, San Jose, CA (US); Michael Edward Hogard, Odessa, FL (US); Gopi K. Lingam, San Jose, CA (US); Shih-Paul Chen, San Jose, CA (US); Dean Hu, San Leandro, CA (US)

(73) Assignee: Outset Medical, Inc., San Jose, CA (US)

( * ) Notice: Subject to any disclaimer, the term of this patent is extended or adjusted under 35 U.S.C. 154(b) by 842 days.

(21) Appl. No.: 16/325,664

(22) PCT Filed: Aug. 21, 2017

(86) PCT No.: PCT/US2017/047791
§ 371 (c)(1),
(2) Date: Feb. 14, 2019

(87) PCT Pub. No.: WO2018/035520
PCT Pub. Date: Feb. 22, 2018

(65) Prior Publication Data
US 2019/0192758 A1 Jun. 27, 2019

Related U.S. Application Data

(60) Provisional application No. 62/377,416, filed on Aug. 19, 2016.

(51) Int. Cl.
*A61M 1/28* (2006.01)
*A61M 1/16* (2006.01)
(Continued)

(52) U.S. Cl.
CPC ............ *A61M 1/287* (2013.01); *A61M 1/168* (2013.01); *A61M 1/1656* (2013.01);
(Continued)

(58) Field of Classification Search
CPC ...... A61M 1/28; A61M 1/287; A61M 1/1656; A61M 1/168; A61M 1/1686;
(Continued)

(56) References Cited

U.S. PATENT DOCUMENTS 1,662,870 A 3/1928 Stancliffe
3,356,360 A 12/1967 Ward
(Continued)

FOREIGN PATENT DOCUMENTS

CA 2887068 A1 4/2014
CA 2930431 A1 5/2015
(Continued)

OTHER PUBLICATIONS

Hogard et al.; U.S. Appl. No. 16/550,042 entitled "Dialysis system and methods," filed Aug. 23, 2019.
(Continued)

*Primary Examiner* — John Kim
(74) *Attorney, Agent, or Firm* — Shay Glenn LLP (57) ABSTRACT

Described herein are systems and methods for performing peritoneal dialysis. According to one aspect, the disclosure provides a sterile interface connection for connecting a water purification system to a disposable source of dialysate concentrates. The sterile interface connection can include a chamber comprising an inlet adapted to be connected to the water purification system on a proximal end and a valve on a distal end. The sterile interface connection can also include spring-loaded needle disposed in the chamber. The spring-loaded needle can move between a retracted configuration in which the spring-loaded needle is fully retracted into the (Continued)

chamber and the valve is closed and sealed, and an extended configuration in which the spring-loaded needle extends through the valve into the disposable source of dialysate concentrates.

11 Claims, 9 Drawing Sheets

(51) Int. Cl.
    *A61M 5/14*         (2006.01)
    *A61M 5/158*       (2006.01)
    *C02F 9/00*         (2006.01)
    *A61M 5/145*       (2006.01)
    *C02F 103/02*      (2006.01)
    *A61M 5/142*       (2006.01)
    *A61M 39/10*       (2006.01)

(52) U.S. Cl.
CPC ............ *A61M 1/1686* (2013.01); *A61M 1/28* (2013.01); *A61M 5/1452* (2013.01); *A61M 5/1454* (2013.01); *A61M 5/158* (2013.01); *C02F 9/00* (2013.01); *A61M 2005/1426* (2013.01); *A61M 2005/14252* (2013.01); *A61M 2005/14268* (2013.01); *A61M 2005/1581* (2013.01); *A61M 2005/1585* (2013.01); *A61M 2039/1066* (2013.01); *A61M 2209/04* (2013.01); *A61M 2209/045* (2013.01); *C02F 2103/026* (2013.01)

(58) Field of Classification Search
CPC .. A61M 5/1452; A61M 5/1454; A61M 5/158; A61M 2005/14252; A61M 2005/1426; A61M 2005/14268; A61M 2005/1581; A61M 2005/1585; A61M 2039/1066; A61M 2209/04; A61M 2209/045; C02F 1/001; C02F 1/283; C02F 1/42; C02F 1/441; C02F 1/444; C02F 9/00; C02F 2103/026

See application file for complete search history.

(56) References Cited

U.S. PATENT DOCUMENTS

| | | |
|---|---|---|
| 3,695,445 A | 10/1972 | Esmond |
| 3,710,237 A | 1/1973 | Watson et al. |
| 3,762,032 A | 10/1973 | Bowling et al. |
| 3,809,309 A | 5/1974 | Batista |
| 3,827,563 A | 8/1974 | Boe et al. |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,110,220 A | 8/1978 | Lavender |
| 4,115,273 A | 9/1978 | Winstead |
| 4,155,157 A | 5/1979 | Gersbacher |
| 4,172,033 A | 10/1979 | Willock |
| 4,194,014 A | 3/1980 | Hermans et al. |
| 4,204,628 A | 5/1980 | Houston et al. |
| 4,209,391 A | 6/1980 | Lipps |
| 4,229,299 A | 10/1980 | Savitz et al. |
| 4,231,366 A | 11/1980 | Schael |
| 4,267,040 A | 5/1981 | Schal |
| 4,293,409 A | 10/1981 | Riede et al. |
| 4,310,416 A | 1/1982 | Tanaka et al. |
| 4,317,725 A | 3/1982 | Kume et al. |
| 4,342,651 A | 8/1982 | Ahrens |
| 4,476,022 A | 10/1984 | Doll |
| 4,486,303 A | 12/1984 | Brous |
| 4,500,426 A | 2/1985 | Ishii et al. |
| 4,508,622 A | 4/1985 | Polaschegg |
| 4,536,201 A | 8/1985 | Brorsson et al. |
| 4,560,472 A | 12/1985 | Granzow et al. |
| 4,624,784 A | 11/1986 | Lefebvre |
| 4,647,748 A | 3/1987 | Glassman |
| 4,661,246 A | 4/1987 | Ash |
| 4,689,108 A | 8/1987 | Barry, Jr. et al. |
| 4,756,835 A | 7/1988 | Wilson |
| 4,769,134 A | 9/1988 | Allan et al. |
| 4,770,787 A | 9/1988 | Heath et al. |
| 4,773,991 A | 9/1988 | Aid |
| 4,786,411 A | 11/1988 | Benattar et al. |
| 4,827,430 A | 5/1989 | Aid et al. |
| 4,869,421 A | 9/1989 | Norris et al. |
| 4,875,619 A | 10/1989 | Anderson et al. |
| 4,889,635 A | 12/1989 | Chevallet |
| 4,894,164 A | 1/1990 | Polaschegg |
| 4,923,613 A | 5/1990 | Chevallet |
| 5,087,930 A | 2/1992 | Roy et al. |
| 5,092,836 A | 3/1992 | Polaschegg |
| 5,094,749 A | 3/1992 | Seita et al. |
| 5,147,605 A | 9/1992 | Tatsuno et al. |
| 5,227,049 A | 7/1993 | Chevallet et al. |
| 5,232,145 A | 8/1993 | Alley et al. |
| 5,236,476 A | 8/1993 | Klick |
| 5,247,434 A | 9/1993 | Peterson et al. |
| 5,259,961 A | 11/1993 | Eigendorf |
| 5,312,550 A | 5/1994 | Hester |
| 5,313,023 A | 5/1994 | Johnson |
| 5,316,676 A | 5/1994 | Drori |
| 5,326,476 A | 7/1994 | Grogan et al. |
| 5,336,165 A | 8/1994 | Twardowski |
| 5,342,326 A | 8/1994 | Peppel et al. |
| 5,344,392 A | 9/1994 | Senninger et al. |
| 5,346,472 A | 9/1994 | Keshaviah et al. |
| 5,360,395 A | 11/1994 | Utterberg |
| 5,385,623 A | 1/1995 | Diaz |
| 5,394,732 A | 3/1995 | Johnson et al. |
| 5,395,351 A | 3/1995 | Munsch |
| 5,401,238 A | 3/1995 | Pirazzoli |
| 5,409,612 A | 4/1995 | Maltais et al. |
| 5,421,208 A | 6/1995 | Packard et al. |
| 5,439,451 A | 8/1995 | Collinson et al. |
| 5,469,264 A | 11/1995 | Shigemori |
| 5,472,614 A | 12/1995 | Rossi |
| 5,489,385 A | 2/1996 | Raabe et al. |
| 5,498,253 A | 3/1996 | Aswad et al. |
| 5,498,338 A | 3/1996 | Kruger et al. |
| 5,503,624 A | 4/1996 | Roeher et al. |
| 5,520,640 A | 5/1996 | Utterberg |
| 5,526,357 A | 6/1996 | Jandrell |
| 5,533,996 A | 7/1996 | Murphey et al. |
| 5,534,328 A | 7/1996 | Ashmead et al. |
| 5,536,258 A | 7/1996 | Folden |
| 5,580,460 A | 12/1996 | Polaschegg |
| 5,580,523 A | 12/1996 | Bard |
| 5,582,600 A | 12/1996 | Loh |
| 5,591,016 A | 1/1997 | Kubota et al. |
| 5,591,344 A | 1/1997 | Kenley et al. |
| 5,593,581 A | 1/1997 | Lescoche |
| 5,595,712 A | 1/1997 | Harbster et al. |
| 5,609,770 A | 3/1997 | Zimmerman et al. |
| 5,610,645 A | 3/1997 | Moore et al. |
| 5,611,214 A | 3/1997 | Wegeng et al. |
| 5,613,663 A | 3/1997 | Schmidt et al. |
| 5,615,996 A | 4/1997 | Suzuki et al. |
| 5,618,268 A | 4/1997 | Raines et al. |
| 5,618,441 A | 4/1997 | Rosa et al. |
| 5,620,608 A | 4/1997 | Rosa et al. |
| 5,623,969 A | 4/1997 | Raines |
| 5,624,572 A | 4/1997 | Larson et al. |
| 5,629,871 A | 5/1997 | Love et al. |
| 5,630,804 A | 5/1997 | Imada et al. |
| 5,643,190 A | 7/1997 | Utterberg |
| 5,647,984 A | 7/1997 | Hovland et al. |
| 5,648,684 A | 7/1997 | Bertin et al. |
| 5,650,071 A | 7/1997 | Brugger et al. |
| 5,662,144 A | 9/1997 | Lo et al. |
| 5,685,835 A | 11/1997 | Brugger |
| 5,689,966 A | 11/1997 | Zess et al. |
| 5,693,008 A | 12/1997 | Brugger et al. |

(56) References Cited

U.S. PATENT DOCUMENTS

| | | |
|---|---|---|
| 5,698,916 A | 12/1997 | Eguchi |
| 5,711,883 A | 1/1998 | Folden et al. |
| 5,713,850 A | 2/1998 | Heilmann et al. |
| 5,725,773 A | 3/1998 | Polaschegg |
| 5,743,892 A | 4/1998 | Loh et al. |
| 5,744,031 A | 4/1998 | Bene |
| 5,749,226 A | 5/1998 | Bowman et al. |
| 5,769,985 A | 6/1998 | Kawakami et al. |
| 5,779,833 A | 7/1998 | Cawley et al. |
| 5,782,575 A | 7/1998 | Vincent et al. |
| 5,788,099 A | 8/1998 | Treu et al. |
| 5,788,851 A | 8/1998 | Kenley et al. |
| 5,792,367 A | 8/1998 | Mattisson et al. |
| 5,811,062 A | 9/1998 | Wegeng et al. |
| 5,813,235 A | 9/1998 | Peterson |
| 5,851,202 A | 12/1998 | Carlsson |
| 5,858,238 A | 1/1999 | Mcrea et al. |
| 5,858,239 A | 1/1999 | Kenley et al. |
| 5,861,555 A | 1/1999 | Hobro et al. |
| 5,868,930 A | 2/1999 | Kopf |
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |
| 5,951,863 A | 9/1999 | Kruger et al. |
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Parris et al. |
| 5,983,947 A | 11/1999 | Utterberg |
| 5,984,903 A | 11/1999 | Nadal |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski et al. |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Olk et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,141 B1 | 9/2001 | Shaldon et al. |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,355,161 B1 | 3/2002 | Shah et al. |
| 6,357,332 B1 | 3/2002 | Vecchio |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Roeher et al. |
| 6,432,309 B1 | 8/2002 | Fuke et al. |
| 6,454,736 B1 | 9/2002 | Ludt et al. |
| 6,454,942 B1 | 9/2002 | Shintani et al. |
| 6,468,056 B1 | 10/2002 | Murakoshi |
| 6,477,058 B1 | 11/2002 | Luebs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,503,062 B1 | 1/2003 | Gray et al. |
| 6,514,225 B1 | 2/2003 | Utterberg et al. |
| 6,514,412 B1 | 2/2003 | Insley et al. |
| 6,526,357 B1 | 2/2003 | Soussan et al. |
| 6,527,728 B2 | 3/2003 | Zhang |
| 6,530,262 B1 | 3/2003 | Esser |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B2 | 6/2003 | Pott et al. |
| 6,582,385 B2 | 6/2003 | Burbank et al. |
| 6,592,558 B2 | 7/2003 | Quah |

(56) References Cited

U.S. PATENT DOCUMENTS

| | | |
|---|---|---|
| 6,601,432 B1 | 8/2003 | Ericson et al. |
| 6,602,424 B1 | 8/2003 | Kramer et al. |
| 6,604,908 B1 | 8/2003 | Bryant et al. |
| 6,607,644 B1 | 8/2003 | Apffel, Jr. |
| 6,607,697 B1 | 8/2003 | Müller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |
| 6,653,841 B1 | 11/2003 | Koerdt et al. |
| 6,654,660 B1 | 11/2003 | Singh et al. |
| 6,666,840 B1 | 12/2003 | Falkvall et al. |
| 6,666,909 B1 | 12/2003 | Tegrotenhuis et al. |
| 6,672,502 B1 | 1/2004 | Paul et al. |
| 6,673,311 B1 | 1/2004 | Sotoyama et al. |
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Dönig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,716,356 B2 | 4/2004 | Collins et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,738,052 B1 | 5/2004 | Manke et al. |
| 6,743,193 B2 | 6/2004 | Brugger et al. |
| 6,744,038 B2 | 6/2004 | Wang et al. |
| 6,746,514 B2 | 6/2004 | Bedingfield et al. |
| 6,749,814 B1 | 6/2004 | Bergh et al. |
| 6,767,333 B1 | 7/2004 | Müller et al. |
| 6,775,577 B2 | 8/2004 | Crnkovich et al. |
| 6,793,831 B1 | 9/2004 | Paul et al. |
| 6,797,056 B2 | 9/2004 | David |
| 6,804,991 B2 | 10/2004 | Balschat et al. |
| 6,806,947 B1 | 10/2004 | Ekdahl et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Vanden Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | Mcherron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,967,002 B1 | 11/2005 | Edgson et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,004,924 B1 | 2/2006 | Brugger et al. |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundtveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,279,134 B2 | 10/2007 | Chan et al. |
| 7,291,123 B2 | 11/2007 | Baraldi et al. |
| 7,306,197 B2 | 12/2007 | Parrino et al. |
| 7,314,061 B2 | 1/2008 | Peppel |
| 7,316,780 B1 | 1/2008 | Fendya et al. |
| 7,337,674 B2 | 3/2008 | Burbank et al. |
| 7,341,568 B2 | 3/2008 | Zhang |
| 7,354,426 B2 | 4/2008 | Young |
| 7,355,685 B2 | 4/2008 | Scibona et al. |
| 7,378,280 B2 | 5/2008 | Quake et al. |
| 7,381,195 B2 | 6/2008 | Mori et al. |
| 7,393,337 B2 | 7/2008 | Tonelli et al. |
| 7,402,249 B2 | 7/2008 | Ikeda |
| 7,469,716 B2 | 12/2008 | Parrino et al. |
| 7,470,265 B2 | 12/2008 | Brugger et al. |
| 7,488,301 B2 | 2/2009 | Beden et al. |
| 7,488,447 B2 | 2/2009 | Sternby |
| 7,493,824 B2 | 2/2009 | Brucksch et al. |
| 7,494,590 B2 | 2/2009 | Felding et al. |
| 7,503,908 B2 | 3/2009 | Bartholomew |
| 7,507,380 B2 | 3/2009 | Chang et al. |
| 7,510,545 B2 | 3/2009 | Peppel |
| 7,517,332 B2 | 4/2009 | Tonelli et al. |
| 7,517,387 B2 | 4/2009 | Chevallet et al. |
| 7,520,919 B2 | 4/2009 | Caleffi |
| 7,537,687 B2 | 5/2009 | Toyoda et al. |

(56) References Cited

U.S. PATENT DOCUMENTS

| | | |
|---|---|---|
| 7,544,300 B2 | 6/2009 | Brugger et al. |
| 7,551,043 B2 | 6/2009 | Nguyen et al. |
| 7,559,911 B2 | 7/2009 | Giannella |
| 7,575,562 B2 | 8/2009 | Oishi et al. |
| 7,575,564 B2 | 8/2009 | Childers |
| 7,591,449 B2 | 9/2009 | Raines et al. |
| 7,603,907 B2 | 10/2009 | Reiter et al. |
| 7,615,035 B2 | 11/2009 | Peppel |
| 7,618,531 B2 | 11/2009 | Sugioka et al. |
| 7,622,043 B2 | 11/2009 | Sawada et al. |
| 7,632,470 B2 | 12/2009 | Tabata et al. |
| 7,647,834 B2 | 1/2010 | O'Mahony et al. |
| 7,648,474 B2 | 1/2010 | Paolini et al. |
| 7,648,476 B2 | 1/2010 | Bock et al. |
| 7,648,792 B2 | 1/2010 | Kaschmitter et al. |
| 7,656,527 B2 | 2/2010 | Scarpaci |
| 7,661,294 B2 | 2/2010 | Dam |
| 7,671,974 B2 | 3/2010 | O'Mahony et al. |
| 7,682,328 B2 | 3/2010 | Han et al. |
| 7,686,778 B2 | 3/2010 | Burbank et al. |
| 7,699,992 B2 | 4/2010 | Sternby |
| 7,708,714 B2 | 5/2010 | Connell et al. |
| 7,713,226 B2 | 5/2010 | Ash et al. |
| 7,726,361 B2 | 6/2010 | Bartholomew |
| 7,727,220 B2 | 6/2010 | Wieslander et al. |
| 7,744,553 B2 | 6/2010 | Kelly et al. |
| 7,749,184 B2 | 7/2010 | Cavalcanti et al. |
| 7,758,082 B2 | 7/2010 | Weigel et al. |
| 7,758,547 B2 | 7/2010 | Tonelli et al. |
| 7,771,379 B2 | 8/2010 | Treu |
| 7,771,380 B2 | 8/2010 | Jönsson et al. |
| 7,775,986 B2 | 8/2010 | Roeher et al. |
| 7,776,219 B2 | 8/2010 | Brugger et al. |
| 7,780,848 B2 | 8/2010 | Kim et al. |
| 7,788,038 B2 | 8/2010 | Oshita et al. |
| 7,790,029 B2 | 9/2010 | Dannenmaier et al. |
| 7,794,141 B2 | 9/2010 | Perry et al. |
| 7,794,419 B2 | 9/2010 | Paolini et al. |
| 7,801,746 B2 | 9/2010 | Moll et al. |
| 7,815,852 B2 | 10/2010 | Sternby |
| 7,824,354 B2 | 11/2010 | Vinci et al. |
| 7,871,390 B2 | 1/2011 | Rambod et al. |
| 7,873,489 B2 | 1/2011 | Dolgos et al. |
| 7,896,831 B2 | 3/2011 | Sternby et al. |
| 7,901,579 B2 | 3/2011 | Brugger et al. |
| 7,913,751 B2 | 3/2011 | Zwittig |
| 7,918,993 B2 | 4/2011 | Harraway |
| 7,922,899 B2 | 4/2011 | Vasta et al. |
| 7,955,504 B1 | 6/2011 | Jovanovic et al. |
| 7,968,250 B2 | 6/2011 | Kaschmitter et al. |
| 8,002,727 B2 | 8/2011 | Brugger et al. |
| 8,012,114 B2 | 9/2011 | Daniel et al. |
| 8,075,509 B2 | 12/2011 | Molducci et al. |
| 8,105,265 B2 | 1/2012 | Demers et al. |
| 8,105,266 B2 | 1/2012 | Childers et al. |
| 8,128,822 B2 | 3/2012 | Browning et al. |
| 8,137,554 B2 | 3/2012 | Jovanovic et al. |
| 8,182,440 B2 | 5/2012 | Cruz et al. |
| 8,182,691 B2 | 5/2012 | Stahl |
| 8,190,651 B2 | 5/2012 | Treu et al. |
| 8,192,387 B2 | 6/2012 | Brugger et al. |
| 8,210,049 B2 | 7/2012 | Brugger |
| 8,235,931 B2 | 8/2012 | Burbank et al. |
| 8,236,599 B2 | 8/2012 | Chang et al. |
| 8,267,881 B2 | 9/2012 | O'Mahony et al. |
| 8,273,245 B2 | 9/2012 | Jovanovic et al. |
| 8,293,113 B2 | 10/2012 | Jönsson et al. |
| 8,293,114 B2 | 10/2012 | Jönsson et al. |
| 8,298,427 B2 | 10/2012 | Ficheux et al. |
| 8,323,492 B2 | 12/2012 | Childers et al. |
| 8,329,030 B2 | 12/2012 | Childers et al. |
| 8,343,085 B2 | 1/2013 | Toyoda et al. |
| 8,394,046 B2 | 3/2013 | Nuernberger et al. |
| 8,414,182 B2 | 4/2013 | Paul et al. |
| 8,419,945 B2 | 4/2013 | Browning et al. |
| 8,425,471 B2 | 4/2013 | Grant et al. |
| 8,449,487 B2 | 5/2013 | Hovland et al. |
| 8,460,228 B2 | 6/2013 | Burbank et al. |
| 8,475,398 B2 | 7/2013 | O'Mahony |
| 8,491,518 B2 | 7/2013 | Schnell et al. |
| 8,496,824 B2 | 7/2013 | Remkes et al. |
| 8,501,009 B2 | 8/2013 | Peterson et al. |
| 8,506,536 B2 | 8/2013 | Schnell |
| 8,512,553 B2 | 8/2013 | Cicchello et al. |
| 8,512,554 B2 | 8/2013 | Yu et al. |
| 8,524,086 B2 | 9/2013 | Peterson et al. |
| 8,529,491 B2 | 9/2013 | Beiriger |
| 8,535,525 B2 | 9/2013 | Heyes et al. |
| 8,603,020 B2 | 12/2013 | Roger et al. |
| 8,608,658 B2 | 12/2013 | Burbank et al. |
| 8,647,290 B2 | 2/2014 | Masala et al. |
| 8,679,348 B2 | 3/2014 | Burbank et al. |
| 8,685,244 B2 | 4/2014 | Heyes et al. |
| 8,685,251 B2 | 4/2014 | Smejtek et al. |
| 8,753,515 B2 | 6/2014 | Curtis et al. |
| 8,801,922 B2 | 8/2014 | Wrazel et al. |
| 8,840,581 B2 | 9/2014 | McGill et al. |
| 9,024,746 B2 | 5/2015 | Burbank et al. |
| 9,097,370 B2 | 8/2015 | Schnell et al. |
| 9,138,687 B2 | 9/2015 | Peterson et al. |
| 9,220,825 B2 | 12/2015 | Buckberry |
| 9,220,828 B2 | 12/2015 | Coates |
| 9,283,320 B2 | 3/2016 | Brugger et al. |
| 9,328,969 B2 | 5/2016 | Wrazel et al. |
| 9,402,945 B2 | 8/2016 | Hogard et al. |
| 9,480,455 B2 | 11/2016 | Buckberry |
| 9,482,218 B2 | 11/2016 | Coates et al. |
| 9,504,777 B2 | 11/2016 | Hogard et al. |
| 9,526,822 B2 | 12/2016 | Meyer et al. |
| 9,545,469 B2 | 1/2017 | Curtis et al. |
| 9,579,440 B2 | 2/2017 | Hogard et al. |
| 9,592,029 B2 | 3/2017 | Buckberry |
| 9,636,444 B2 | 5/2017 | Burbank et al. |
| 9,700,663 B2 | 7/2017 | Burbank et al. |
| 9,835,509 B2 | 12/2017 | Brugger et al. |
| 9,879,807 B2 | 1/2018 | Brugger et al. |
| 9,895,480 B2 | 2/2018 | Wrazel et al. |
| 10,105,476 B2 | 10/2018 | Peterson et al. |
| 10,155,076 B2 | 12/2018 | Merchant |
| 2002/0023879 A1 | 2/2002 | Hadden |
| 2002/0032398 A1 | 3/2002 | Steele et al. |
| 2002/0108859 A1 | 8/2002 | Wang et al. |
| 2002/0108869 A1 | 8/2002 | Savtchenko |
| 2002/0115200 A1 | 8/2002 | Zou et al. |
| 2002/0162784 A1 | 11/2002 | Kohlheb et al. |
| 2002/0187069 A1 | 12/2002 | Levin et al. |
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0138349 A1 | 7/2003 | Robinson et al. |
| 2003/0156991 A1 | 8/2003 | Halas et al. |
| 2003/0163077 A1 | 8/2003 | Kim et al. |
| 2003/0183345 A1 | 10/2003 | Soberay |
| 2003/0220598 A1 | 11/2003 | Busby et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0020286 A1 | 2/2004 | Blakley et al. |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0072278 A1 | 4/2004 | Chou et al. |
| 2004/0084370 A1 | 5/2004 | Singh et al. |
| 2004/0084371 A1 | 5/2004 | Kellam et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |

(56) References Cited

U.S. PATENT DOCUMENTS

| | | |
|---|---|---|
| 2005/0007748 A1 | 1/2005 | Callahan et al. |
| 2005/0040110 A1 | 2/2005 | Felding |
| 2005/0070837 A1 | 3/2005 | Ferrarini et al. |
| 2005/0074834 A1 | 4/2005 | Chaplen et al. |
| 2005/0082225 A1 | 4/2005 | Kreymann |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2006/0046113 A1 | 3/2006 | Wang et al. |
| 2006/0079698 A1 | 4/2006 | Joshi et al. |
| 2006/0157413 A1 | 7/2006 | Bene et al. |
| 2006/0174715 A1 | 8/2006 | Wehrs et al. |
| 2006/0200064 A1 | 9/2006 | Gross et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0149914 A1 | 6/2007 | Axelsson et al. |
| 2007/0158249 A1 | 7/2007 | Ash |
| 2007/0158268 A1 | 7/2007 | Decomo |
| 2007/0184576 A1 | 8/2007 | Chang et al. |
| 2007/0215644 A1 | 9/2007 | Otis et al. |
| 2007/0243990 A1 | 10/2007 | Kolenbrander et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |
| 2008/0053842 A1 | 3/2008 | Williams et al. |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichiishi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1 | 2/2009 | Chaung et al. |
| 2009/0076433 A1 | 3/2009 | Folden et al. |
| 2009/0087326 A1 | 4/2009 | Voltenburg et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0230036 A1 | 9/2009 | Apel et al. |
| 2009/0306573 A1 | 12/2009 | Gagner et al. |
| 2009/0309835 A1 | 12/2009 | Levin et al. |
| 2009/0312686 A1 | 12/2009 | Sakamoto et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0089807 A1 | 4/2010 | Heyes et al. |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0292657 A1 | 11/2010 | Fontanazzi et al. |
| 2010/0292944 A1 | 11/2010 | Howell et al. |
| 2010/0321046 A1 | 12/2010 | Randall et al. |
| 2010/0326914 A1 | 12/2010 | Drost et al. |
| 2011/0005986 A1 | 1/2011 | Kelly et al. |
| 2011/0105979 A1 | 5/2011 | Schlaeper et al. |
| 2011/0106466 A1 | 5/2011 | Furmanski et al. |
| 2011/0132841 A1 | 6/2011 | Rohde et al. |
| 2011/0186517 A1 | 8/2011 | Hedmann et al. |
| 2011/0189048 A1 | 8/2011 | Curtis et al. |
| 2011/0257579 A1 | 10/2011 | Rossi et al. |
| 2011/0295175 A1 | 12/2011 | Felder et al. |
| 2012/0029937 A1 | 2/2012 | Neftel et al. |
| 2012/0065581 A1 | 3/2012 | Childers et al. |
| 2012/0103902 A1 | 5/2012 | Childers et al. |
| 2012/0138533 A1 | 6/2012 | Curtis et al. |
| 2012/0204968 A1 | 8/2012 | Fulkerson et al. |
| 2012/0226236 A1 | 9/2012 | Fini et al. |
| 2012/0267291 A1 | 10/2012 | Coates |
| 2012/0292246 A1 | 11/2012 | Jovanovic et al. |
| 2012/0298580 A1 | 11/2012 | Gronau et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0030344 A1 | 1/2013 | Gronau et al. |
| 2013/0037485 A1 | 2/2013 | Wilt et al. |
| 2013/0056418 A1 | 3/2013 | Kopperschmidt et al. |
| 2013/0056419 A1 | 3/2013 | Curtis |
| 2013/0060233 A1 | 3/2013 | O'Connor et al. |
| 2013/0146541 A1 | 6/2013 | Weigel et al. |
| 2013/0180339 A1 | 7/2013 | Brugger |
| 2013/0186829 A1 | 7/2013 | Callan et al. |
| 2013/0206693 A2 | 8/2013 | Thys |
| 2013/0213890 A1 | 8/2013 | Kelly et al. |
| 2013/0267883 A1 | 10/2013 | Medrano |
| 2013/0303962 A1 | 11/2013 | Bernard |
| 2013/0303963 A1 | 11/2013 | Breuch et al. |
| 2014/0014580 A1 | 1/2014 | Ritter |
| 2014/0018727 A1 | 1/2014 | Burbank et al. |
| 2014/0021111 A1 | 1/2014 | Roger et al. |
| 2014/0069861 A1 | 3/2014 | Browning et al. |
| 2014/0072288 A1 | 3/2014 | Newell |
| 2014/0076058 A1 | 3/2014 | Brugger et al. |
| 2014/0158589 A1 | 6/2014 | Furuhashi et al. |
| 2014/0178215 A1 | 6/2014 | Baxter et al. |
| 2014/0209540 A1 | 7/2014 | Smejtek et al. |
| 2014/0276424 A1 | 9/2014 | Davis et al. |
| 2014/0291243 A1 | 10/2014 | Curtis et al. |
| 2014/0319035 A1 | 10/2014 | Burbank et al. |
| 2015/0005699 A1 | 1/2015 | Burbank et al. |
| 2015/0027951 A1 | 1/2015 | Wallace et al. |
| 2015/0041377 A1 | 2/2015 | Heyes |
| 2015/0076053 A1 | 3/2015 | Higgitt et al. |
| 2015/0129481 A1 | 5/2015 | Higgitt et al. |
| 2015/0196702 A1 | 7/2015 | Burbank et al. |
| 2015/0204733 A1 | 7/2015 | Newell et al. |
| 2015/0238676 A1 | 8/2015 | Giordano et al. |
| 2015/0252800 A1 | 9/2015 | Buckberry et al. |
| 2015/0267821 A1 | 9/2015 | Brugger et al. |
| 2015/0306294 A1 | 10/2015 | Jansson et al. |
| 2015/0314055 A1 | 11/2015 | Hogard et al. |
| 2015/0343128 A1 | 12/2015 | Hogard et al. |
| 2015/0343133 A1 | 12/2015 | Hogard et al. |
| 2015/0354906 A1 | 12/2015 | Miller |
| 2015/0359973 A1 | 12/2015 | Onken et al. |
| 2016/0051739 A1 | 2/2016 | Buckberry |
| 2016/0051743 A1 | 2/2016 | Buckberry |
| 2016/0082172 A1 | 3/2016 | Miller et al. |
| 2016/0084785 A1 | 3/2016 | Buckberry |
| 2016/0106906 A1 | 4/2016 | Buckberry |
| 2016/0199558 A1 | 7/2016 | Buckberry |
| 2016/0325034 A1 | 11/2016 | Wiktor et al. |
| 2017/0290970 A1 | 10/2017 | Friederichs et al. |
| 2017/0296727 A1 | 10/2017 | Burbank et al. |
| 2017/0296730 A1 | 10/2017 | Soto et al. |
| 2017/0312419 A1 | 11/2017 | Burbank et al. |
| 2017/0326285 A1 | 11/2017 | Hogard et al. |
| 2018/0071447 A1 | 3/2018 | Gronau et al. |
| 2018/0104400 A1 | 4/2018 | Burbank et al. |
| 2018/0126056 A1 | 5/2018 | Wrazel et al. |
| 2018/0128688 A1 | 5/2018 | Newell et al. |
| 2018/0128698 A1 | 5/2018 | Brugger et al. |
| 2019/0022293 A1 | 1/2019 | Peterson et al. |
| 2021/0069401 A1 | 3/2021 | Peterson et al. |
| 2022/0040389 A1 | 2/2022 | Hogard et al. |

(56) References Cited

U.S. PATENT DOCUMENTS

| | | | |
|---|---|---|---|
| 2022/0143285 | A1 | 5/2022 | Hu et al. |
| 2022/0203004 | A1 | 6/2022 | Hu et al. |

FOREIGN PATENT DOCUMENTS

| | | |
|---|---|---|
| CN | 200951223 Y | 9/2007 |
| DE | 8702995 U1 | 6/1987 |
| DE | 69217519 T2 | 6/1997 |
| EP | 0165751 A2 | 12/1985 |
| EP | 0324922 A2 | 7/1989 |
| EP | 0679100 A1 | 11/1995 |
| EP | 0796997 A1 | 9/1997 |
| EP | 0547025 B2 | 6/2002 |
| EP | 1892000 A1 | 2/2008 |
| EP | 1898000 A2 | 3/2008 |
| EP | 2319551 A2 | 5/2011 |
| EP | 2535067 A1 | 12/2012 |
| GB | 1289738 A | 9/1972 |
| JP | 59-58002 A | 4/1984 |
| JP | 60-143803 A | 7/1985 |
| JP | H4-35669 A | 2/1992 |
| JP | H11-33111 A | 2/1999 |
| JP | 2001510266 A | 7/2001 |
| JP | 2002143298 A | 5/2002 |
| JP | 2002527212 A | 8/2002 |
| JP | 2003508179 A | 3/2003 |
| JP | 2007167108 A | 7/2007 |
| JP | 2007268490 A | 10/2007 |
| JP | 2007529707 A | 10/2007 |
| JP | 2007327950 A | 12/2007 |
| JP | 2012152286 A | 8/2012 |
| JP | 55-14045 A | 6/2014 |
| JP | 2014531922 A | 12/2014 |
| JP | 2018524074 A | 8/2018 |
| WO | WO00/16916 A1 | 3/2000 |
| WO | WO00/25843 A1 | 5/2000 |
| WO | WO00/57935 A1 | 10/2000 |
| WO | WO02/40874 A1 | 5/2002 |
| WO | WO02/076529 A1 | 10/2002 |
| WO | WO03/076661 A1 | 9/2003 |
| WO | WO2006/011009 A2 | 2/2006 |
| WO | WO2006/039293 A2 | 4/2006 |
| WO | WO2007/073739 A1 | 7/2007 |
| WO | WO2007/089855 A2 | 8/2007 |
| WO | WO2008/027967 A1 | 3/2008 |
| WO | WO2008/106191 A2 | 9/2008 |
| WO | WO2010/027435 A1 | 3/2010 |
| WO | WO2010/062698 A2 | 6/2010 |
| WO | WO2010/085764 A2 | 7/2010 |
| WO | WO2010/146343 A2 | 12/2010 |
| WO | WO2013/031966 A1 | 3/2013 |
| WO | WO2014/117000 A2 | 7/2014 |
| WO | WO2014/124180 A2 | 8/2014 |
| WO | WO2014/159420 A1 | 10/2014 |
| WO | WO2014/160370 A1 | 10/2014 |
| WO | WO2015/150179 A1 | 10/2015 |
| WO | WO2015/173151 A1 | 11/2015 |
| WO | WO2015/185920 A1 | 12/2015 |
| WO | WO2016/030147 A1 | 3/2016 |
| WO | WO2016/049542 A2 | 3/2016 |
| WO | WO2016/057981 A1 | 4/2016 |
| WO | WO2016/057982 A1 | 4/2016 |
| WO | WO2016/130679 A2 | 9/2016 |
| WO | WO2017/072511 A1 | 5/2017 |
| WO | WO2018/035520 A1 | 2/2018 |

OTHER PUBLICATIONS

Hogard et al.; U.S. Appl. No. 17/244,672 entitled "Dialysis system and methods," filed Apr. 29, 2021.

Hogard et al.; U.S. Appl. No. 17/244,684 entitled "Dialysis system and methods," filed Apr. 29, 2021.

Allis et al., "Chapter 16: Nanostructural Architectures from Molecular Building Blocks," in Handbook of Nanoscience, Engineering, and Technology, 1st Edition (Electrical Engineering Handbook), CRC Press LLC, Boca Raton, FL, Chapter 16 (70 pgs.), Oct. 2002.

Anglés et al., "Plasticized starch/Tunicin Whiskers Nanocomposite Materials. 2. Mechanical behavior," Macromolecules, 34, pp. 2921-2931, Mar. 2001.

California Energy Commission; Development of Supported Polymeric Liquid Membrane Technology for Aqueous MTBE Mitigation, EPRI, Palo Alto, CA, California Energy Commission, Sacramento, CA: Doc. No. 1006577; 70 pgs.; Jul. 2002.

Demura et al., "Ductile Thin Foil of Ni3Al," Mechanical Properties of Structural Films, ASTM International Nov. 2000 Symposium (Orlando, FL), pp. 248-261, published Oct. 1, 2001.

Favier et al.; Nanocomposite materials from latex and cellulose whiskers; Polymers for Advanced Technologies; 6; pp. 351-355; Jan. 1995.

Federal Energy Technology Center, "Technology Development Through Industrial Partnerships," (Tech. Dev. Data Sheet), 12 pgs., Sep. 1998.

Grunert et al., "Progress in the Development of Cellulose Reinforced Nanocomposites," PMSE Preprints 2000, 82, 232, 2 pgs., Mar. 2000.

Haas, "Further development of MMW and SMMW platelet feed horn arrays," Astron. Soc. Pac. Conf. Ser., vol. 75, pp. 99-105, Multi-Feed Systems for Radio Telescopes, Workshop held in Tucson, Arizona, May 16-18, 1994.

Introtek International; Drip chamber liquid level sensor (sales literature); 2 pages; retrieved from the internet (http://www.introtek.com/PDFs/1/DDS-14.0_DripDetectSensor.pdf); © Jan. 1, 2009.

Koeneman et al., "Feasibility of Micro Power Supplies for MEMS," (pre-publication copy) J. MicroElectoMechanical Sys., 6(4), pp. 355-362, Dec. 1997.

Morin et al., "Nanocomposites of Chitin Whiskers from Riftia Tubes and Poly (caprolactone)," Macromolecules, vol. 35, pp. 2190-2199, Feb. 2002.

Nakamura et al., "Research on Pressure Welding Conditions of Various Work Metals (Effects of Contact Pressure, Surface Expansion Ratio and Temperature)," JSME International Journal, Series III 31(3), 612-617, Sep. 1988.

Nakao et al., "Diffusion Bonding of Intermetallic Compound TiAl," ISIJ International, 31(10), 1260-1266, Oct. 1991.

Oddy et al., "Electrokinetic Instability Micromixing," Anal. Chem., 73(24), pp. 5822-5832, Dec. 2001.

Omega Engineering Inc.; Load Cell (definition, information); 3 pgs; retrieved from the internet on Jun. 17, 2015 (http://www.omega.com/prodinfo/LoadCells.html).

Orts et al., "Effect of Fiber Source on Cellulose Reinforced Polymer Nanocomposites," ANTEC 2004: Conference Proceedings, 62nd Annual Tech. Conference; Chicago, IL, pp. 2427-2431, May 2004.

Paillet et al., "Chitin Whisker Reinforced Thermoplastic Nanocomposites," Macromolecules, vol. 34, No. 19, pp. 6527-6530, Sep. 2001.

Paul et al., "Microlamination for Microtechnology-based Energy, Chemical, and Biological Systems," ASME IMECE, ASE vol. 39, pp. 45-52, Nashville, Tennessee, Nov. 15-20, 1999.

Pluess, "Application of Controlled Thermal Expansion in Diffusion Bonding for the High-Volume Microlamination of MECS Devices," Thesis (MS), Oregon State University, 193 pgs., Sep. 2004.

Porter et al.; Cost drivers in microlamination based on a high volume production system design; ASME 2002 Conf. Proc.; New Orleans, Louisiana; pp. 267-274; Nov. 17-22, 2002.

Sharma et al., "The Application of Surface Mount Technology to Multi-Scale Process Intensification," ASPE, pp. 1-4, Oct. 2003.

Stroock et al., "Chaotic Mixer for Microchannels," Science, 295, pp. 647-651, Jan. 2002.

Thorsen et al.; Microfluidic Large-Scale Integration; Science; 298; pp. 580-584; Oct. 18, 2002.

Wegeng et al., "Chemical system miniaturization," Proceedings of the AIChE Spring National Meeting, pp. 1-13, Feb. 1996.

Hogard et al.; U.S. Appl. No. 16/295,676 entitled "Dialysis System and Methods," filed Mar. 7, 2019.

PERITONEAL DIALYSIS SYSTEM AND METHODS

CROSS REFERENCE TO RELATED APPLICATIONS

This application claims the benefit of U.S. Provisional Appln. No. 62/377,416, filed Aug. 19, 2016, titled "Peritoneal Dialysis System and Methods", which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to dialysis systems. More specifically, this disclosure relates to peritoneal dialysis systems that include many features that reduce the need for disposables storage by using on-demand water and making setup and delivery easier for the patient.

BACKGROUND

There are, at present, hundreds of thousands of patients in the United States with end-stage renal disease. Most of those require dialysis to survive. Many patients receive hemodialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Peritoneal dialysis provides an alternative to hemodialysis in which fluid is introduced into the peritoneum through a permanent tube in the abdomen. Peritoneal dialysis is typically performed in a patient's home while the patient sleeps. The main complication from peritoneal dialysis is infection of the abdomen through the permanent tube.

Traditional peritoneal dialysis requires the batch preparation of fluid that is terminally sterilized before being consumed by the patient. In addition, traditional peritoneal dialysis systems require the patient to make numerous fluid connections. This batch preparation of fluid and numerous setup steps makes treatment in the home difficult.

SUMMARY

Described herein are apparatus including a sterile interface connection configured to connect a water purification system to a disposable source of dialysate concentrates, the sterile interface connection comprising a chamber comprising an inlet adapted to be connected to the water purification system on a proximal end and a valve on a distal end, a spring-loaded needle disposed in the chamber, a proximal end of the spring-loaded needle being connected to the inlet, wherein the sterile interface connection includes a retracted configuration in which the spring-loaded needle is fully retracted into the chamber and the valve is closed and sealed, the sterile interface connection further including an extended configuration in which the spring-loaded needle extends through the valve into the disposable source of dialysate concentrates.

The spring-loaded needle may further include a lumen extending therethrough and a port disposed at a distal end of the spring-loaded needle. The spring-loaded needle may also be configured to deliver water from the water purification system to the disposable source of dialysate concentrates.

The chamber may further comprise an outlet, the sterile interface connection being configured to, in the retracted position, receive fluid from the water purification system via the inlet to sterilize the chamber and the spring-loaded needle and discard the fluid through the outlet. The fluid may be configured to contact all interior and exterior surfaces of the spring-loaded needle.

Described herein are apparatus including a sterile interface connection of a disposable source of dialysate concentrates, the sterile interface connection being configured to receive a needle of a water purification system to mate the water purification system to the disposable source of dialysate concentrates, the sterile interface connection comprising an alignment feature adapted to guide the needle into the sterile interface connection, a disinfectant plug adjacent to the alignment feature, the disinfectant plug being configured to sterilize the needle as it passes through the disinfectant plug, and a sealing septum adjacent to the disinfectant plug, the sealing septum adapted to form a seal around the needle when the needle punctures the sealing septum.

The interface connection can include a sterile seal disposed over the disinfectant plug, wherein the sterile seal is to be removed from the sterile interface connection prior to needle entry.

Described herein are methods, including a method of connecting a water purification system to a disposable source of dialysate concentrates, comprising receiving a sterile interface connection comprising a chamber, a spring-loaded needle disposed in the chamber, and a valve of the chamber that is closed and sealed, connecting an inlet of the sterile interface connection to the water purification system, extending the spring-loaded needle through the valve into the disposable source of dialysate concentrates.

Any of the methods may further comprise delivering fluid from the water purification system to the disposable source of dialysate concentrates through the sterile interface connection.

Any of the methods may further comprise receiving fluid from the water purification system via an inlet in the sterile interface connection to sterilize the chamber and the spring-loaded needle. Additionally, the methods may include discarding the fluid through an outlet of the sterile interface connection. The fluid can contact all interior and exterior surfaces of the spring-loaded needle.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Some embodiments can include a sterile vessel.

DETAILED DESCRIPTION

This disclosure describes systems, devices, and methods related to peritoneal dialysis therapy. In some embodiments, the peritoneal dialysis system can be a home dialysis system. Embodiments of the dialysis system can include various features that automate and improve the performance, efficiency, and safety of dialysis therapy.

In some embodiments, a dialysis system is described that can provide acute and chronic peritoneal dialysis therapy to users. The system can include a water purification system configured to prepare water for use in dialysis therapy in real-time using available water sources, and a disposable consumable that interfaces with the water purification system to produce dialysate for dialysis therapy.

In some embodiments, a peritoneal dialysis system can prepare substantially sterile water in real-time for creating dialysis solution. The peritoneal dialysis systems described can also include features that make it easy for a patient to self-administer therapy. For example, a disposable consumable with minimal connection points can be easily installed for automated mixing and movement of fluids. Methods of use are also provided, including real-time dialysis solution monitoring, recirculation of dialysis solutions, and interface connections.

Figure 1:
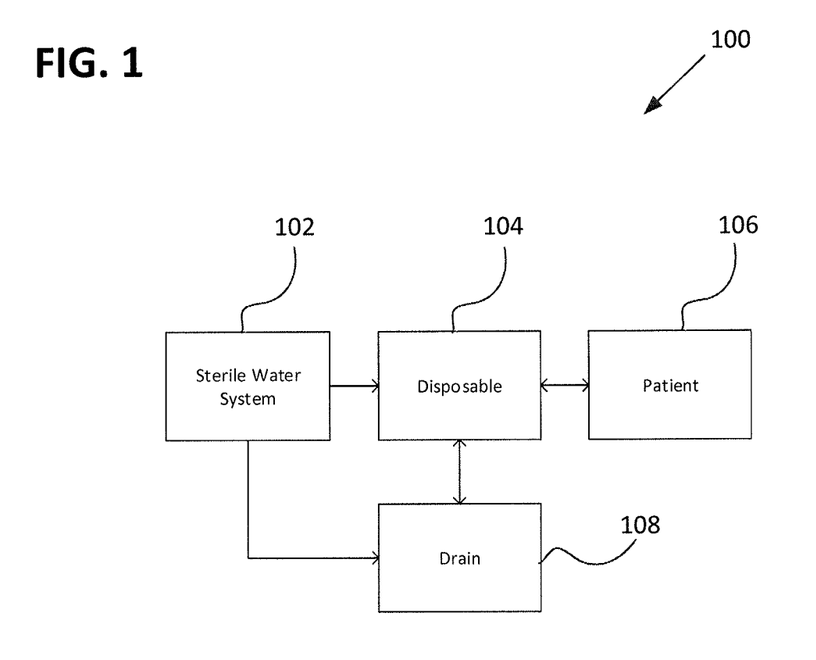
FIG. 1 illustrates one embodiment of a peritoneal dialysis system.

FIG. 1 illustrates one embodiment of a peritoneal dialysis system 100 configured to provide dialysis treatment to a user in either a clinical or non-clinical setting, such as the user's home. The dialysis system 100 can comprise a sterile water system 102 connected to a disposable consumable 104. The disposable consumable 104 can interface with a catheter in the abdomen of the patient 106. Both the sterile water system and the disposable consumable can be connected to a drain 106.

The water purification system 102 can be configured to purify a water source in real-time for dialysis therapy. For example, the water purification system can be connected to a residential water source (e.g., tap water) and prepare pasteurized water in real-time. The pasteurized water can then be used for peritoneal dialysis therapy without the need to heat and cool large batched quantities of water typically associated with water purification methodologies.

Figure 2:
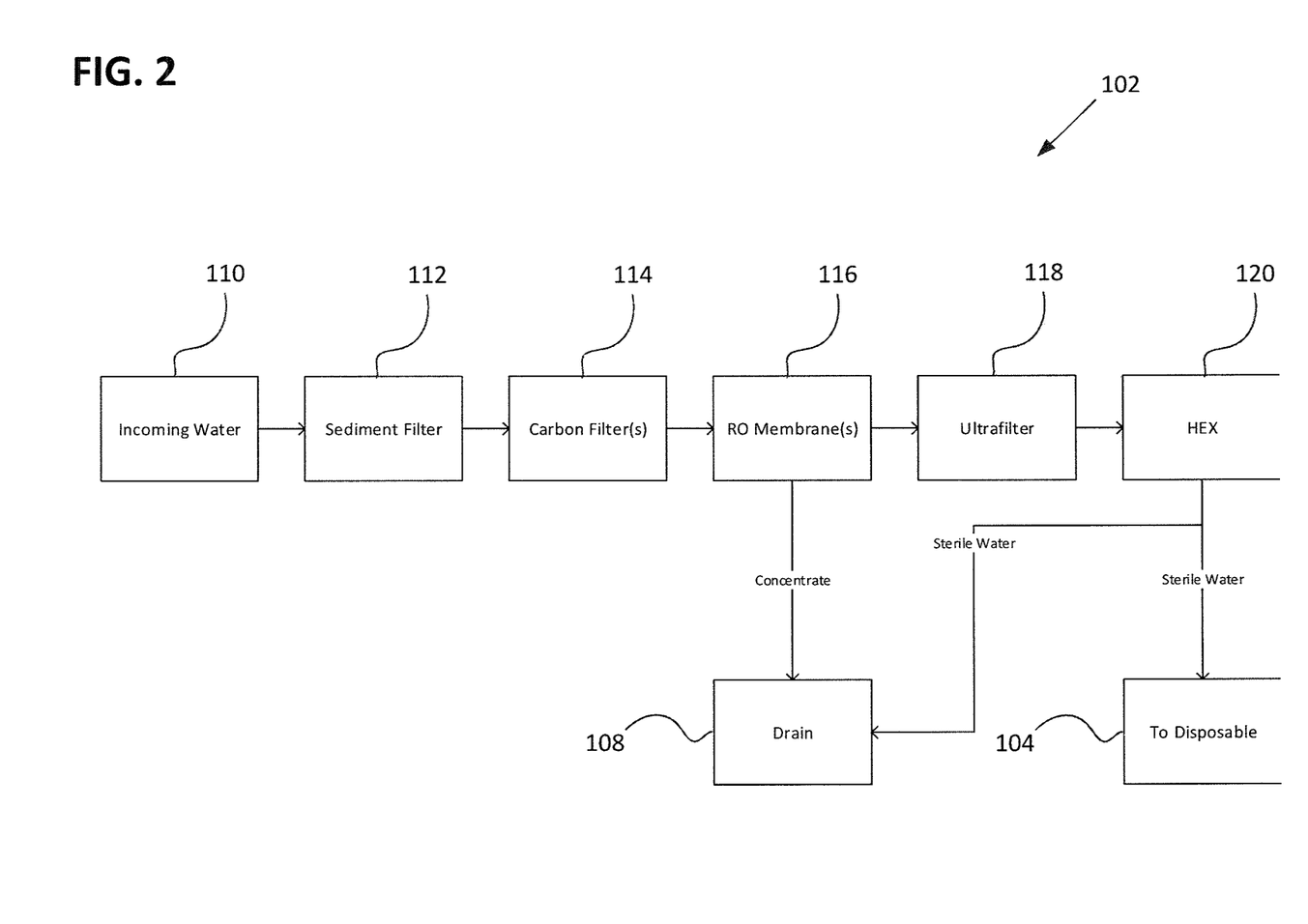
FIG. 2 shows a schematic diagram of the water purification system 102 of FIG. 1.

FIG. 2 shows a schematic diagram of the water purification system 102 of FIG. 1. The water purification system can include a source of incoming water 110 (e.g., a tap), one or more sediment filter(s) 112, carbon filter(s) 114, reverse-osmosis (RO) membrane(s) 116, ultrafilter(s) 118, and a heat exchanger (HEX) 120.

The source of incoming water 110 provides supply water to the water purification system, which passes through the sediment filter(s) 112 to filter out particulates in the fluid.

Next, the fluid passes through the carbon filter(s) 114 to filter toxins such as chlorine and chloramine. In some embodiments, there could be multiple carbon filters to ensure that chlorine and chloramine levels are within acceptable range for downstream components.

The fluid then passes through the RO membranes 116 which reject ions in the fluid. A preferred rejection ratio of the RO membranes can be at least 94%. In other embodiments, the rejection ratio can be at least 90%. The permeate water continues toward the ultrafilter 118, while the concentrated ions removed from the fluid by the RO membranes are directed to the drain 108. In some embodiments, there can be a plurality of RO membranes to maximize permeate water retention.

As the permeate water traverses across the ultrafilter(s) 118, any bacteria or endotoxins adhere to the ultrafilter(s). In one specific embodiment, the ultrafilter can be a polysulfone membrane with a pore size of at least 0.01 microns. In some embodiments, there can be several ultrafilters in series to ensure water purity. In other embodiments, the ultrafilter(s) may be located at other points in the fluid path, including before the RO membranes.

Finally, the permeate water is passed through a pasteurization system or HEX 120, that uses elevated pressures and temperatures to denatured and inactivate all the endotoxins in the permeate water. It has been shown that elevating endotoxin to a temperature above 200 C at a pressure of 240 PSI can provide more than a log 2 reduction in endotoxin level.

Figure 3:
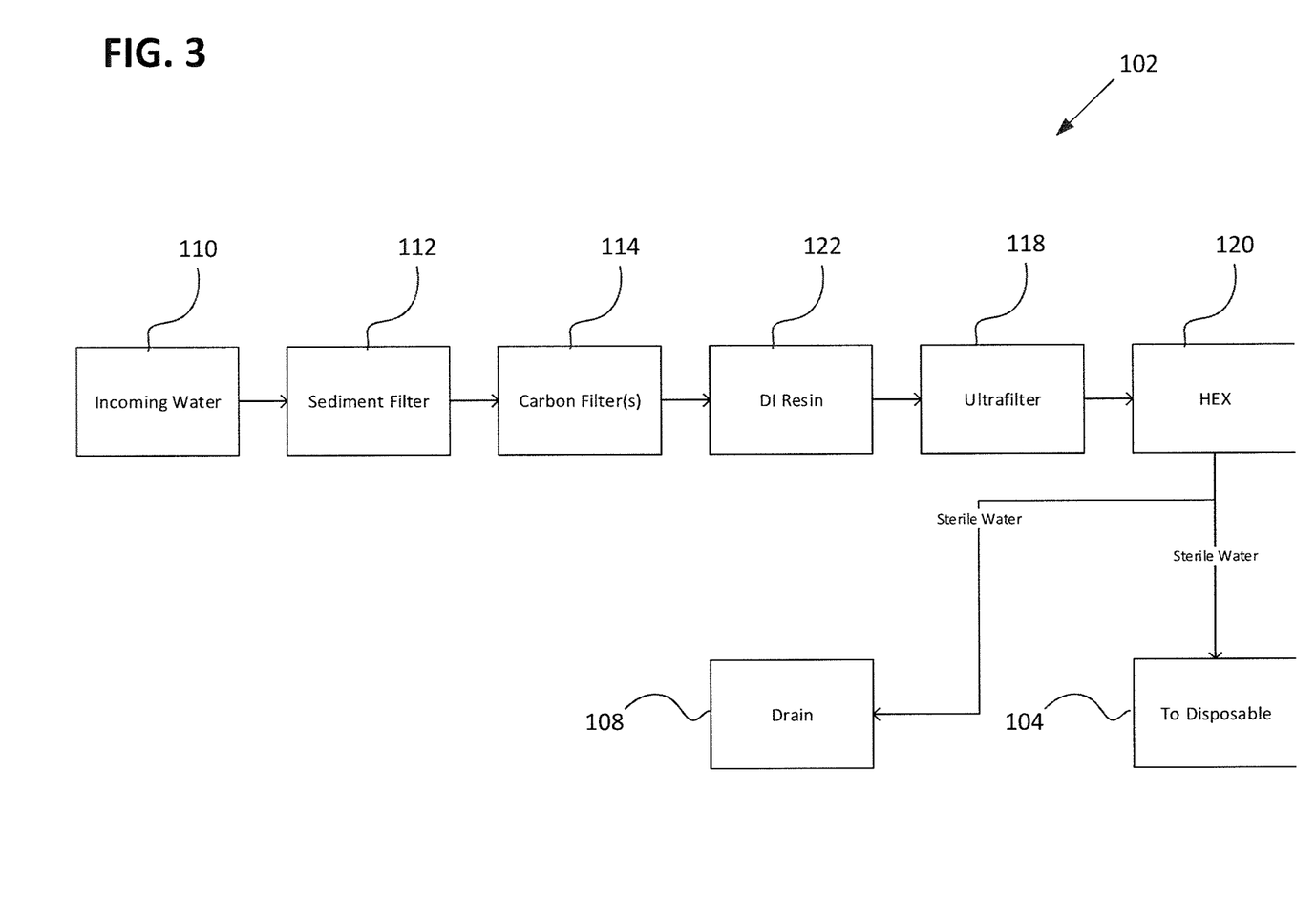
FIG. 3 shows a schematic diagram of an alternate water purification system that uses de-ionization technology to remove ionic impurities prior to the ultrafilter.

FIG. 3 shows a schematic diagram of an alternate water purification system that uses de-ionization technology to remove ionic impurities prior to the ultrafilter. Instead of using RO membranes before the ultrafilter as in the embodiment of FIG. 2, the water purification system 102 of FIG. 3 incorporates one or more de-ionizing resin(s) 122 to capture undesired ions and output pure water.

Once sterile water device reaches temperature and pressure conditions in which endotoxins and bacteria are actively denatured and inactivated, the water can be directed from the water purification system to the disposable consumable. The disposable consumable can include a number of features, described below.

In another embodiment, the sterile water coming from the water purification system can be stored into a sterile vessel. The vessel can be self-disinfectable from water produced by the heat exchanger, and may contain actuator elements to circulate fluid within itself to prevent dead volumes from occurring. In some embodiments, the sterile vessel may be one open volume, wherein contained fluid may be periodically or continuously agitated by one or a plurality of rotary mixers. In one embodiment, a sterile vessel may comprise a substantially non-branched fluid path arranged in a serpentine configuration, or other configuration which allows for a long linear path length in a small volume. One or more circulation pumps disposed within the fluid paths cause the fluid to circulate. The inlet and outlet of the fluid path may be controllably opened by valves to allow water in and out of the fluid path. Sterile water emerging from the vessel can then be mixed with the contents of the concentrate container in a homogenous fashion, and be raised to patient temperature.

Figure 4:
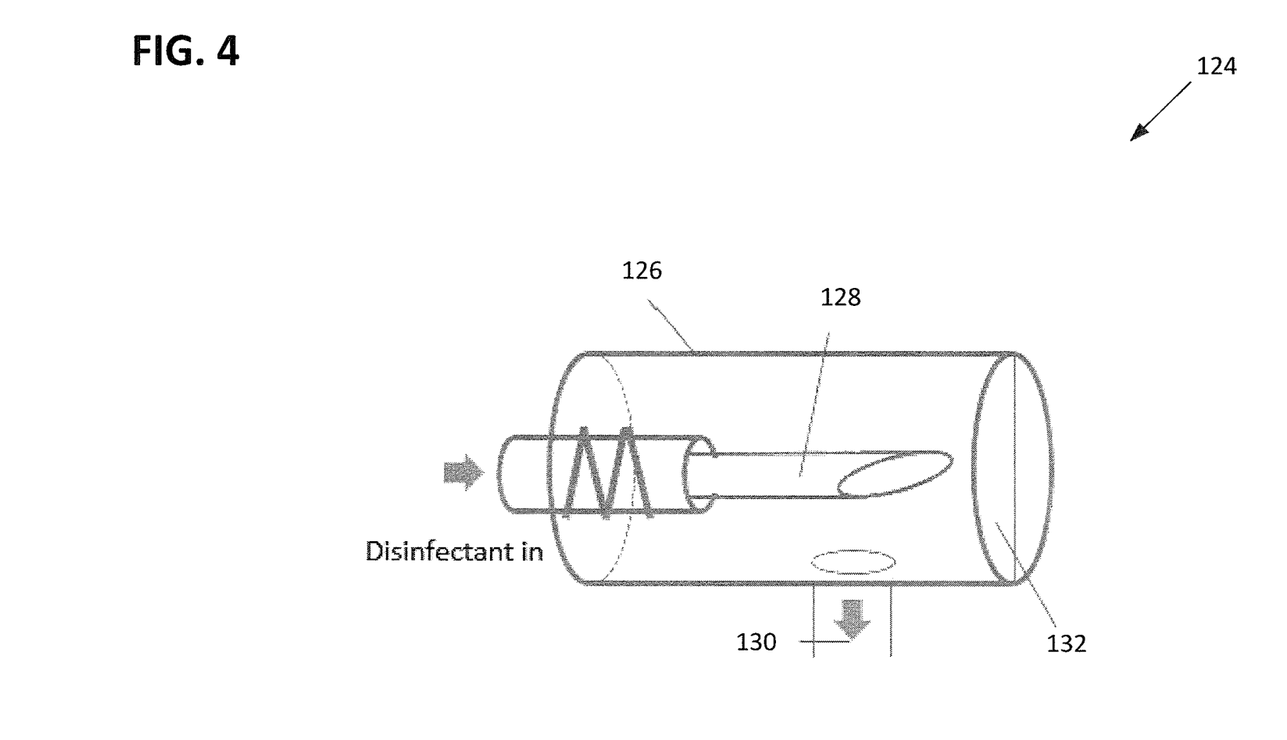
FIG. 4 illustrates a reusable portion of a sterile interface connection that bridges the water purification system to the disposable consumable.
Figure 5:
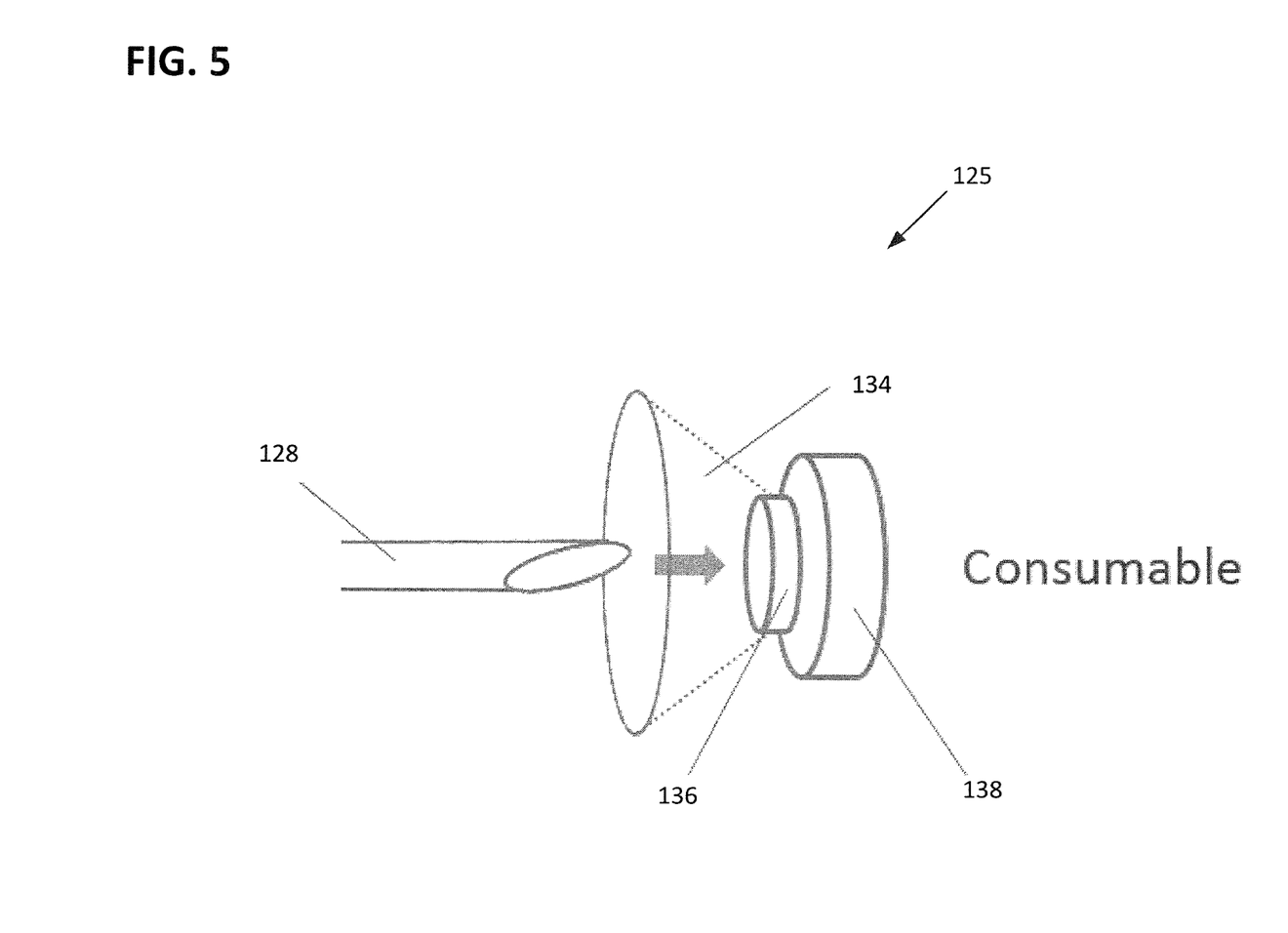
FIGS. 5 and 6 show a disposable portion of the sterile interface connection that bridges the water purification system to the disposable consumable.
Figure 6:
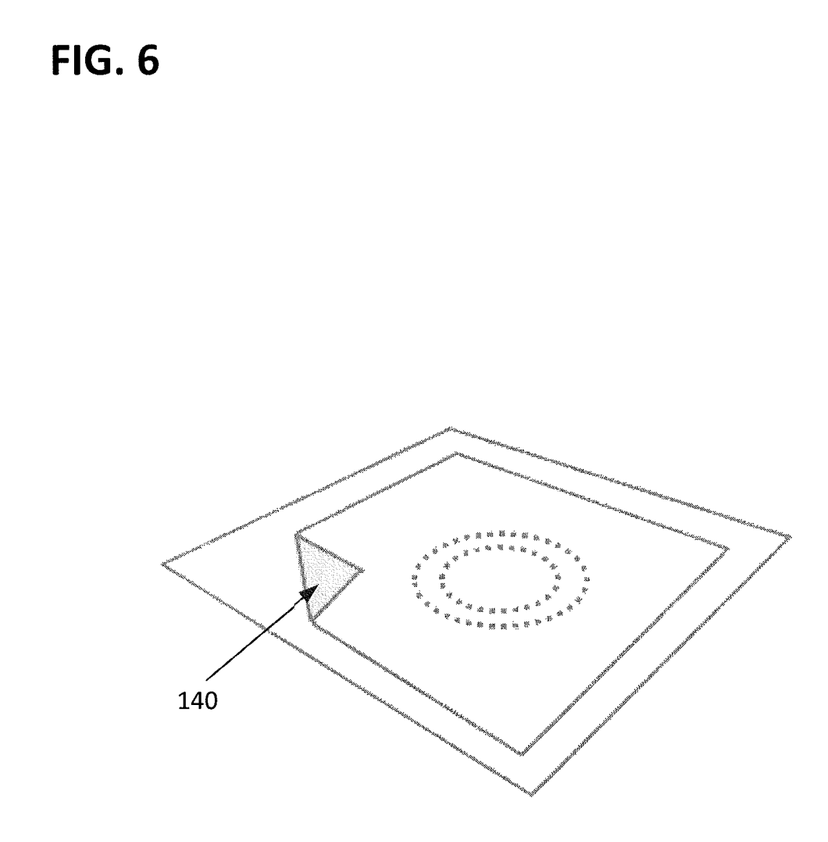

FIGS. 4-6 illustrate a reusable portion of a sterile interface connection that bridges the water purification system to the disposable consumable. The sterile interface connection can include a reusable connection 124 on the water purification system, and a disposable connection 125 on the disposable consumable. The chances for contamination in the peritoneal dialysis system are limited by having only one interface between the disposable consumable and the water purification system.

Referring to FIG. 4, the reusable connection 124 can include a chamber 126, a spring loaded needle 128, a chamber outlet 130, and a self-opening and self-sealing door 132. The reusable connection 124 can include a retracted configuration and an extended configuration. In the retracted configuration, the spring loaded needle 128 can be retracted into the chamber 126 through the door 132 to limit exposure to the ambient environment. In this retracted position, the water purification system can to rinse the interface with disinfectant, sterile water, or a combination of the two. In the extended configuration, the spring loaded needle 128 can extend through the door 132 to puncture or be inserted into the disposable consumable.

Referring to FIGS. 5-6, the disposable connection 125 of the sterile interface connection can have a puncture point that is be pre-sterilized until active use. The puncture point can be manually exposed or automatically exposed prior to active use. In one embodiment, referring to FIG. 5, the puncture point of the disposable connection 125 may include an alignment feature 134 configured to guide needle 128 into the puncture point. In the illustrated embodiment, the puncture point can include a disinfectant plug 136 and a sealing septum 138. The sealing septum can comprise an elastomer or similar material. Upon needle puncture, the sealing septum 138 can form a seal around the needle 128, thereby creating a non-leaking connection between the sterile water system and the disposable.

In another embodiment, referring to FIG. 6, the puncture point can be covered with a sterile seal 140 that is removable by the user prior to active use. Peeling the removable seal may be manual or automatic in nature, but sterility of the puncture point can be maintained.

Systems and methods are also provided for the creation, disposal, and recycling of dialysate solution prior to, during, and after treatment.

Figure 7:
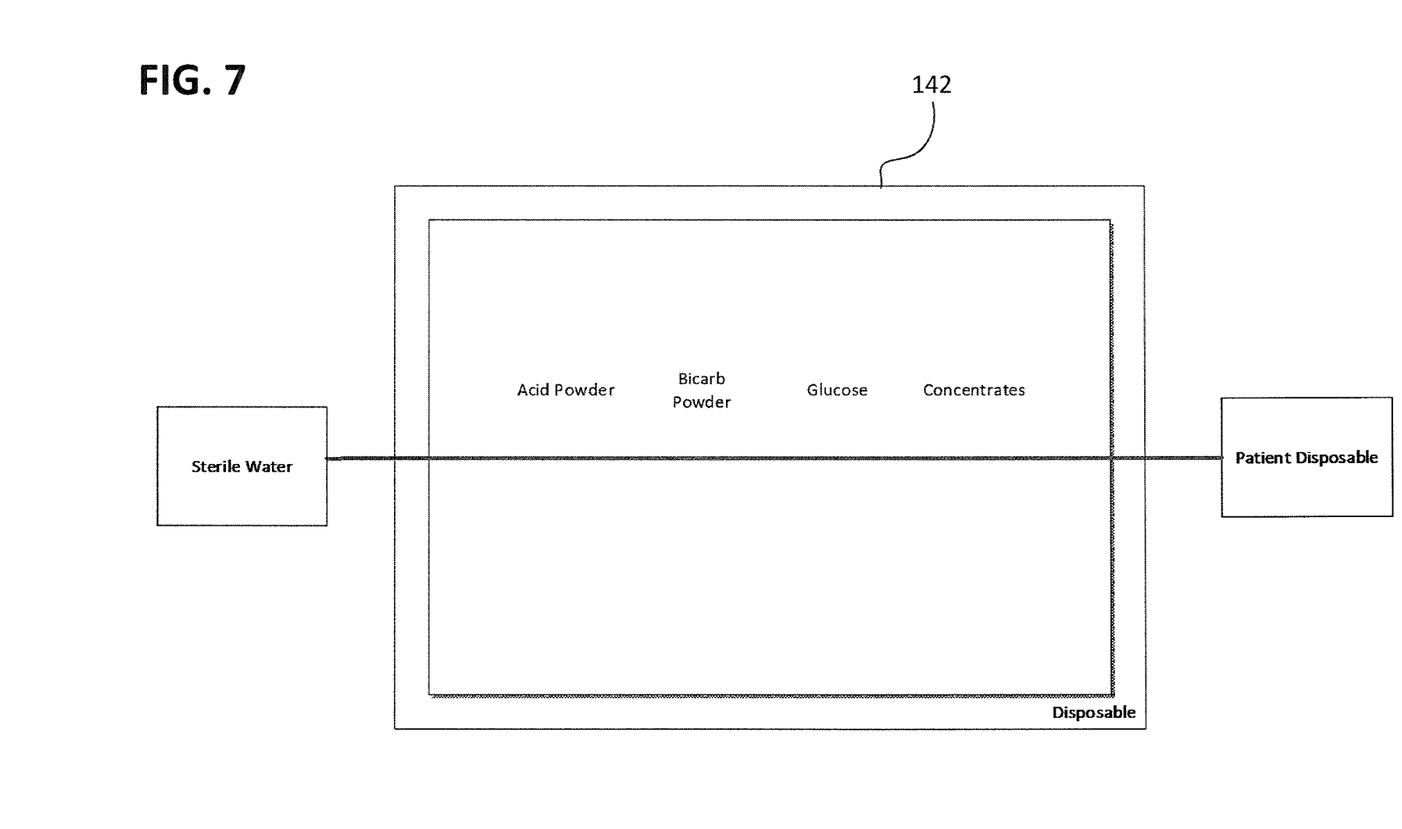
FIG. 7 illustrates a concentrate container that contains pre-sterilized dialysate concentrates proportioned to the appropriate dosage for treatment.

Referring to FIG. 7, the disposable consumable can include a concentrate container 142 that contains pre-sterilized dialysate concentrates proportioned to the appropriate dosage for treatment. In one embodiment, the concentrate container can include acid powder, bicarb powder, glucose, and other concentrates. In some embodiments, these concentrates can be used to produce the oncotic or osmotic gradient required for conducting peritoneal dialysis. In some embodiments, these concentrates may contain high molecular weight substances such as polysaccharide, polyamides or polypeptides in order to minimize transfer of these substances into the patient. Over the course of a typical overnight peritoneal dialysis session, several infusion/drain cycles may be performed, wherein the peritoneal dialysis fluid is infused into the patient's peritoneum, allowed to dwell, and drained. Because there a plurality of concentrates available, the composition of the dialysis fluid infused for each cycle may be varied, for example, to achieve different clinical goals, such as increased fluid removal, minimization of glucose retention, or maintenance of nutritional compounds that may be lost during the drain cycle. In some embodiments, the disposable consumable may have electrodes built into it, connectable to an external sensor for real-time dialysis fluid monitoring.

Sterile water coming from the water purification system can be mixed with the contents of the concentrate container in a homogenous fashion, and be raised to patient temperature. In some embodiments, the disposable consumable comprises two thin, thermally conductive, flexible sheets welded together in a pattern to produce tortuous flow paths that promote mixing of fluids. The disposable consumable may further comprise tubing sections, or other features which can be acted upon by non fluid-contacting pumps on the durable portion of the invention. Temperature, conductivity or other properties of the fluid within the disposable consumable may be sensed or measured by non-contact sensors connected to the durable portion of the invention. Heat may also be applied to the fluid in the disposable consumable through at least one side of the thin, thermally conductive flexible sheets.

Once fully mixed, the dialysis solution could then be routed to a patient with an automated cycler, thereby enabling real-time peritoneal dialysis solution generation and delivery. The benefit of real-time peritoneal dialysis solution generation during automated peritoneal dialysis is such that the patient does not have to make multiple connections from multiple sources, thus increasing the risk of peritonitis. Furthermore, the use of batch prepared dialysis solution can be burdensome for the patient, as bags containing liters of solution are relatively heavy for the typical dialysis patient. This system minimizes intense physical activity for the patient prior to initiating a treatment.

In another embodiment, the fully mixed dialysis solution could then be routed to a sterile dialysis fluid vessel via an automated cycler. This would enable batching of the peritoneal dialysis solution prior to delivery.

Figure 8:
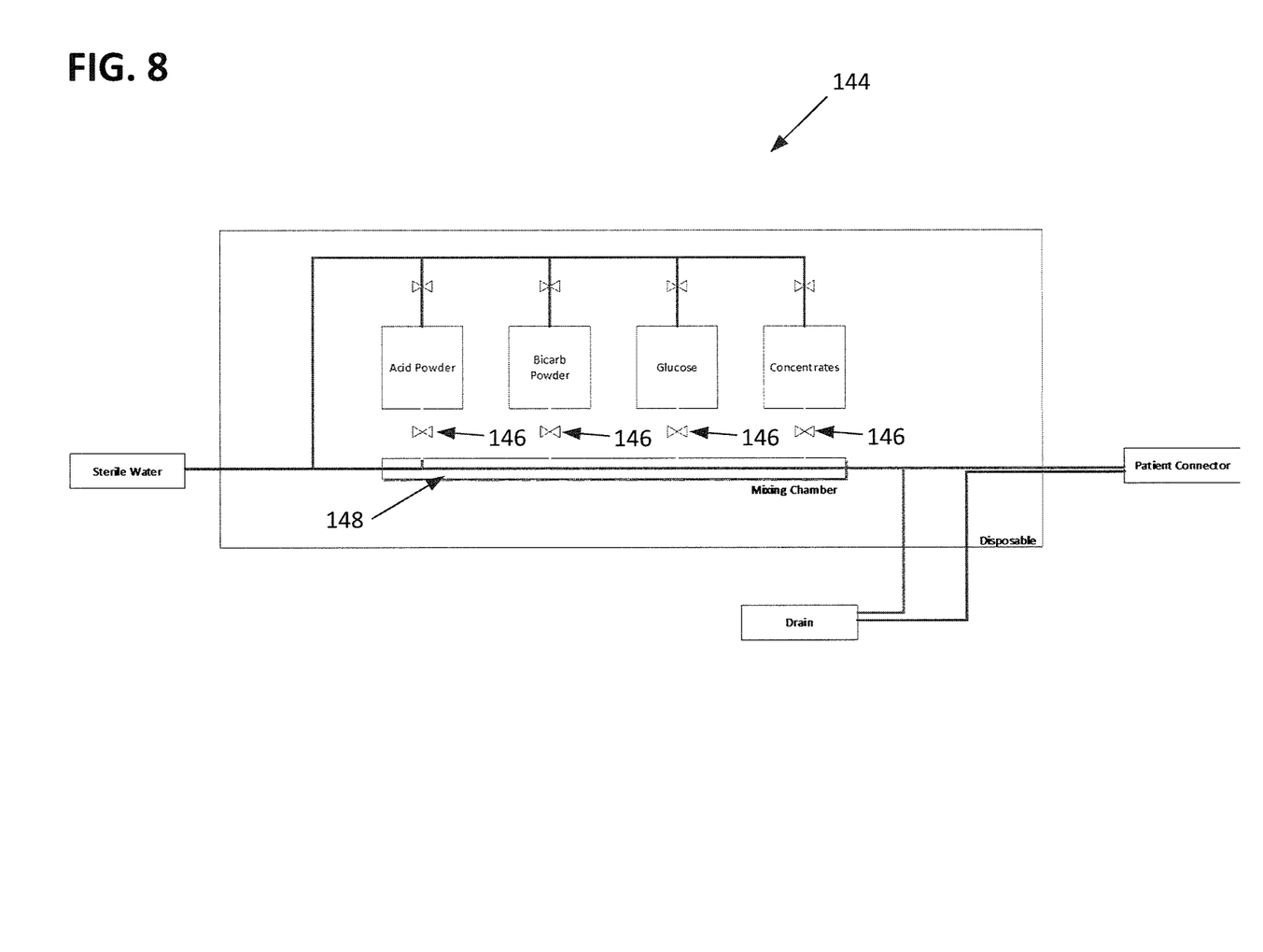
FIG. 8 illustrates an automated cycler of a peritoneal dialysis system which feeds the dialysis solution to and from the patient's peritoneum.

FIG. 8 illustrates an automated cycler 144 of the disposable consumable of a peritoneal dialysis system, which feeds the dialysis solution to and from the patient's peritoneum. The automated cycler 144 can contain all of the non-contact pumps and sensors that interact with the dialysate solution to deliver the solution to the patient. When the spring loaded needle of the reusable connection is connected to the disposable connection, as described above, the internal concentrate lines 146 can be opened. Pumps of the automated cycler, such as peristaltic pumps, can be used to pump supersaturated mixtures of each concentrate into a mixing chamber 148. The fluid within the mixing chamber can then be elevated to the patient temperature.

As proportioning of the dialysis solution is critical, a conductivity sensor will mate to the electrical leads of the disposable consumable to allow the cycler to monitor the quality of the dialysis fluid in real-time. Should the dialysis fluid not meet the settings prescribed on the prescription, the cycler will be able to route the fluid to drain until proportioning is corrected. The conductivity sensor can be placed, for example, at an outlet of the mixing chamber.

Figure 9:
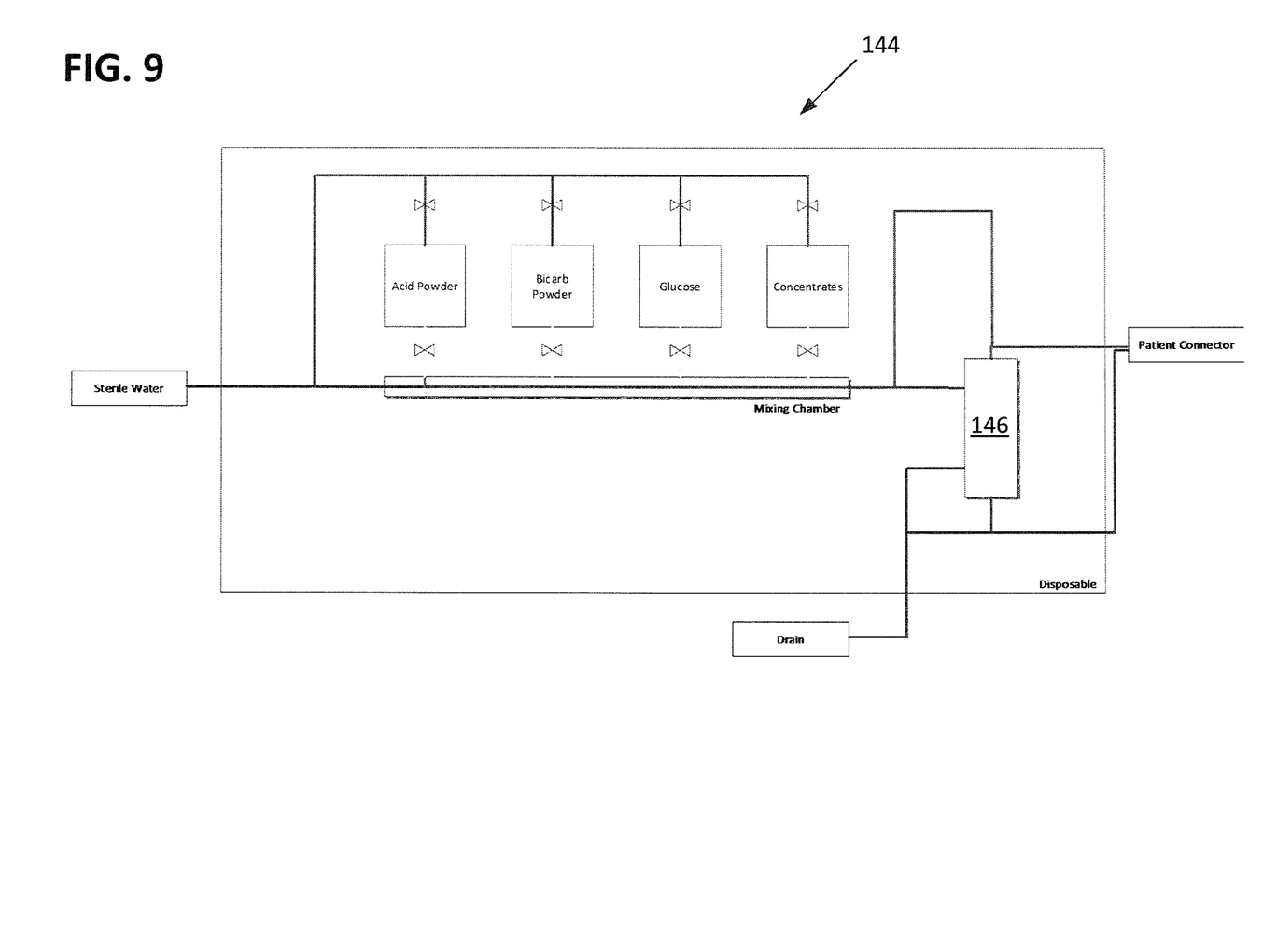
FIG. 9 shows an automated cycler that incorporates a dialyzer.

As extreme nutrient loss is extremely prevalent in peritoneal dialysis, it may be desirable to recycle the patient effluent dialysis solution as to prevent critical proteins from leaving the body. Referring to FIG. 9, the automated cycler 144 can incorporate a dialyzer 146 that allows for the diffusion or convection of waste from one fluid source to another. In this embodiment, the dialysis solution side of the dialyzer can be constantly be replenished with new dialysis solution flowing in one direction, while the patient effluent solution side of the dialyzer can move fluid in the opposite direction as to maximize waste clearances. The dialyzer may also be bypassed, in events for filling or draining the peritoneum.

As peritonitis is a common, yet unexpected, outcome of peritoneal dialysis, early detection of peritonitis symptoms can be detected through the constant monitoring of drain line. In particular, a turbidity meter to monitor patient effluent can be placed in or around the drain line to monitor the change in discoloration of the fluid. Once detected, the automated cycler can alarm the user of the onset of peritonitis and take appropriate action.

What is claimed is:

1. A sterile interface connection configured to connect a water purification system to a disposable source of dialysate concentrates, the sterile interface connection comprising:
    a chamber comprising an inlet adapted to be connected to the water purification system on a proximal end and a self-sealing and self-opening valve on a distal end; and
    a spring-loaded needle disposed in the chamber, a proximal end of the spring-loaded needle being connected to the inlet;
    wherein the sterile interface connection includes a retracted configuration in which the spring-loaded needle is fully retracted into the chamber and the valve is closed and self-sealed, the sterile interface connection further including an extended configuration in which the valve is configured to self-open and the spring-loaded needle extends through the opened valve into the disposable source of dialysate concentrates.

2. The sterile interface connection of claim 1, wherein the spring-loaded needle further comprises a lumen extending therethrough and a port disposed at a distal end of the spring-loaded needle.

3. The sterile interface connection of claim 2, wherein the spring-loaded needle is configured to deliver water from the water purification system to the disposable source of dialysate concentrates.

4. The sterile interface connection of claim 1, wherein the chamber further comprises an outlet, the sterile interface connection being configured to, in the retracted position, receive fluid from the water purification system via the inlet to sterilize the chamber and the spring-loaded needle and discard the fluid through the outlet while the valve is closed.

5. The sterile interface connection of claim 4, wherein when the sterile interface connection receives the fluid to sterilize the chamber and the spring-loaded needle, the spring-loaded needle is positioned such that the fluid contacts all interior and exterior surfaces of the spring-loaded needle.

6. The sterile interface connection of claim 1, wherein the valve comprises a self-sealing and self-opening door.

7. A method of connecting a water purification system to a disposable source of dialysate concentrates, comprising:
    receiving a sterile interface connection comprising a chamber, a spring-loaded needle disposed in the chamber, and a valve of the chamber that is closed and sealed;
    connecting an inlet of the sterile interface connection to the water purification system;
    opening the valve of the chamber; and
    extending the spring-loaded needle through the opened valve into the disposable source of dialysate concentrates.

8. The method of claim 7, further comprising delivering fluid from the water purification system to the disposable source of dialysate concentrates through the sterile interface connection.

9. The method of claim 7, further comprising receiving fluid from the water purification system via an inlet in the sterile interface connection to sterilize the chamber and the spring-loaded needle.

10. The method of claim 9, further comprising discarding the fluid through an outlet of the sterile interface connection while the valve is closed and sealed.

11. The method of claim 9, wherein the fluid contacts all interior and exterior surfaces of the spring-loaded needle.

* * * * *